United States Patent
Blackford et al.

(10) Patent No.: US 7,852,465 B1
(45) Date of Patent: Dec. 14, 2010

(54) SYSTEM FOR MEASURING LIQUID FLOW RATES

(75) Inventors: David B. Blackford, North Oaks, MN (US); Frederick R. Quant, Shoreview, MN (US); Derek R. Oberreit, Roseville, MN (US)

(73) Assignee: Fluid Measurement Technologies, Inc., White Bear Lake, MN (US)

( * ) Notice: Subject to any disclaimer, the term of this patent is extended or adjusted under 35 U.S.C. 154(b) by 0 days.

(21) Appl. No.: 12/857,779

(22) Filed: Aug. 17, 2010

Related U.S. Application Data

(62) Division of application No. 11/935,810, filed on Nov. 6, 2007, now Pat. No. 7,777,868.

(60) Provisional application No. 60/857,548, filed on Nov. 7, 2006.

(51) Int. Cl.
*G01N 1/00* (2006.01)
*G01N 15/02* (2006.01)

(52) U.S. Cl. .................. 356/37; 356/335; 356/336; 73/61.72; 73/865.5; 436/36; 436/164

(58) Field of Classification Search .......... 356/37, 356/335–343; 422/73, 103, 110; 73/61.71, 73/28.02, 865.5, 61.72; 436/36, 164
See application file for complete search history.

(56) References Cited

U.S. PATENT DOCUMENTS

| | | | |
|---|---|---|---|
| 3,563,090 A | 2/1971 | Deltour | |
| 4,181,130 A | 1/1980 | Bailey | |
| 4,314,484 A | 2/1982 | Bowman | |
| 4,583,975 A | 4/1986 | Pekkarinen et al. | |
| 4,673,820 A | 6/1987 | Kamen | |
| 4,680,977 A | 7/1987 | Conero et al. | |
| 4,827,766 A | 5/1989 | Nelson | |
| 4,936,828 A | 6/1990 | Chiang | |
| 4,958,529 A * | 9/1990 | Vestal | 73/864.81 |
| 5,045,069 A | 9/1991 | Imparato | |
| 5,152,424 A | 10/1992 | Weinreb et al. | |
| 5,186,057 A | 2/1993 | Everhart | |
| 5,247,842 A * | 9/1993 | Kaufman et al. | 73/865.5 |
| 5,278,626 A * | 1/1994 | Poole et al. | 356/36 |
| 5,331,309 A | 7/1994 | Sakai | |
| 5,411,052 A | 5/1995 | Murray | |
| 5,982,289 A | 11/1999 | Kingsley et al. | |
| 6,620,620 B1 * | 9/2003 | Anderson et al. | 436/55 |
| 6,640,649 B1 | 11/2003 | Paz et al. | |
| 7,267,121 B2 * | 9/2007 | Ivri | 128/203.17 |
| 7,414,255 B1 | 8/2008 | Amend et al. | |
| 2008/0137065 A1 * | 6/2008 | Oberreit et al. | 356/37 |
| 2009/0183554 A1 * | 7/2009 | Grant et al. | 73/61.71 |
| 2009/0227939 A1 | 9/2009 | Mernoe et al. | |

\* cited by examiner

*Primary Examiner*—Hoa Q Pham
(74) *Attorney, Agent, or Firm*—Haugen Law Firm PLLP; Frederick W. Niebuhr

(57) ABSTRACT

A system for monitoring non-volatile residue concentrations in ultra pure water includes a nebulizer for generating an aerosol composed of multiple water droplets, a heating element changing the aerosol to a suspension of residue particles, and a condensation particle counter to supersaturate the dried aerosol to cause droplet growth through condensation of a liquid onto the particles. The nebulizer incorporates a flow dividing structure that divides exiting waste water into a series of droplets. The droplets are counted to directly indicate a waste water flow rate and indirectly indicate an input flow rate of water supplied to the nebulizer. The condensation particle counter employs water as the condensing medium, avoiding the need for undesirable chemical formulations and enabling use of the ultra pure water itself as the condensing medium.

27 Claims, 7 Drawing Sheets

SYSTEM FOR MEASURING LIQUID FLOW RATES

Figure 1:
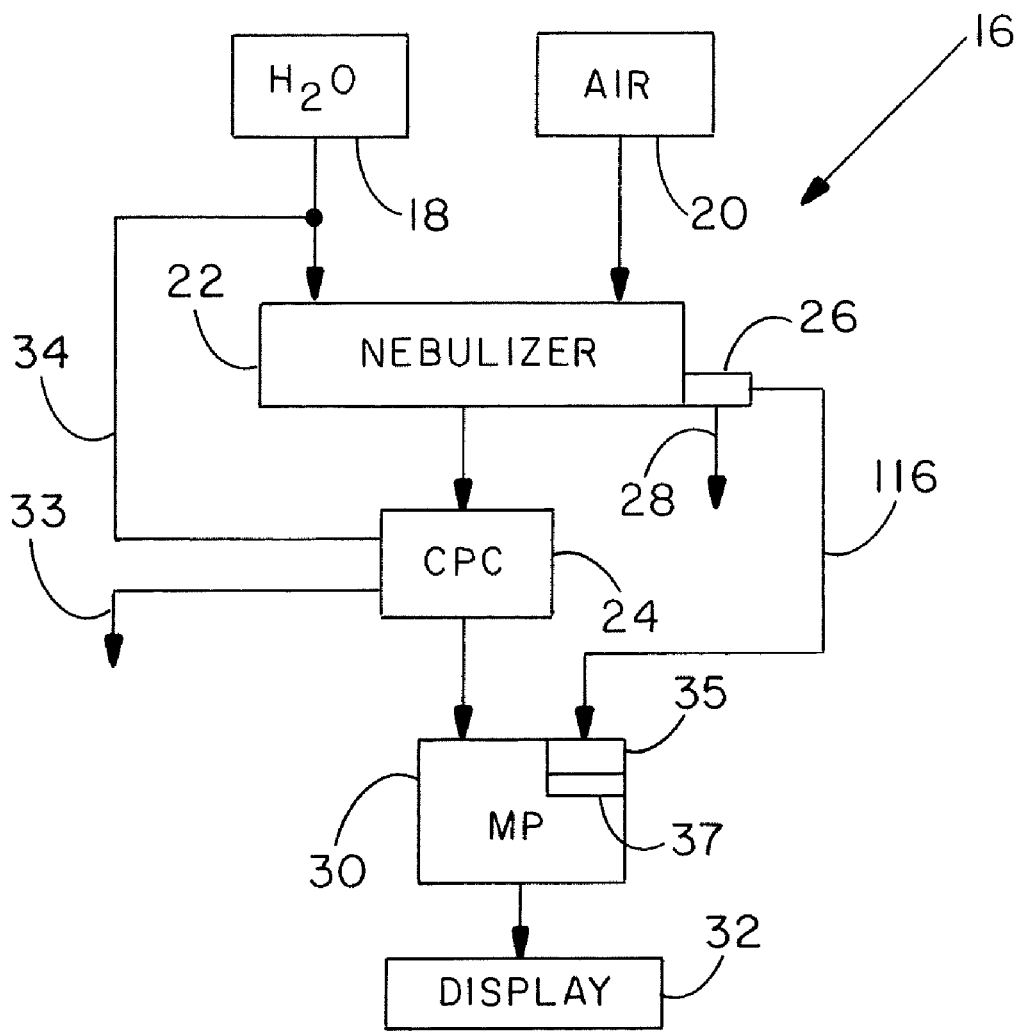

This application is a divisional of U.S. Non-Provisional patent application Ser. No. 11/935,810 entitled "System for Measuring Non-Volatile Residue in Ultra Pure Water," filed Nov. 6, 2007, now U.S. Pat. No. 7,777,868.

This application claims the benefit of priority based on Provisional Application No. 60/857,548 entitled "System for Measuring Non-Volatile Residue in Ultra Pure Water" filed Nov. 7, 2006.

BACKGROUND OF THE INVENTION

The present invention relates to instruments for measuring minute concentrations of impurities in liquids, and more particularly to systems for detecting non-volatile residue concentrations in ultra pure water and aerosol generating components used in such systems.

Certain industries, most notably semiconductor fabrication, involve extremely high standards of cleanliness and purity. A semiconductor component may require washing with ultra pure water after each processing stage, to remove chemicals used in that stage. More generally, ultra pure water may be used to clean fixtures and other tools used to handle semiconductor wafers and other components. Any non-volatile residue present in the ultra pure water can remain on the surface of the component after the water has evaporated, possibly causing defects in the resulting semiconductor device. Thus, there is a need to monitor the ultra pure water used in such processes, to insure that the concentration of non-volatile residue remains at or below acceptable levels.

Systems have been developed and employed successfully to continuously monitor the quality of ultra pure water. U.S. Pat. No. 5,098,657 (Blackford et al.) discloses a system in which ultra pure water is provided at a constant flow rate to a nebulizer where the water is formed into droplets. The droplets are dried to provide non-volatile residue particles. The particles can be detected electrostatically or provided to a condensation particle counter (CPC, also known as a condensation nucleus counter) where the particles are "grown" into larger droplets and sensed optically. Droplets are grown with a fluid having a relatively low vapor mass diffusivity, e.g. butyl alcohol.

While such systems have enjoyed success, they also are subject to difficulties that limit their utility. One of these concerns is measuring the flow rate of the ultra pure water to the nebulizer. Such measurement is critical, because any change in the flow rate, e.g. due to a blockage in the water delivery system, seriously disrupts measurement of the residue concentration. The conventional approach is to position a rotometer just upstream of the nebulizer. Rotometers are not particularly well suited for measuring the extremely low flow rates involved, typically about 1 milliliter per minute. They are expensive, in part due to the need for ultra-clean materials such as Teflon to minimize residue contamination that would adversely affect concentration readings.

Another problem is the accumulation of waste water in the nebulizer. Conventional devices have employed sponges to absorb waste water, but this only postpones the eventual need to remove the waste water.

Another difficulty concerns the sapphire orifice plate typically used to control the flow rate of water into the nebulizer. A forty micron diameter orifice through the plate limits the flow and admits water into the nebulizer. The pressure drop across the orifice plate is sufficient to cause gasses dissolved in the water to accumulate on the back side of the orifice plate and form bubbles. Downstream of the nebulizer, the bubbles eventually break free and tend to disrupt residue concentration measurements.

As to the condensation particle counter, a concern relates to the use of butyl alcohol or similar fluids with low vapor mass diffusivity for growing the residue particles into droplets. Such liquids tend to be flammable, toxic, and produce noxious odors that frequently require vapor exhaust systems to be located near the measuring device. Frequently the liquids are subject to health and environmental regulations that restrict their use in indoor environments. In addition, the liquids require equipment for supplying, collecting and draining the liquid involved.

Another persistent problem is the relatively long time elapsed between a change in the concentration of non-volatile residue in the ultra pure water, and the detection of the change. This raises the risk that contaminated water may be used in several process stages before the condition is realized.

Accordingly, the present invention has several aspects directed to one or more of the following objects:

to provide an aerosol generating device, e.g. a nebulizer, with a reliable means for measuring an input flow rate of the liquid supplied to the device without contacting or otherwise interfering with the liquid used to generate the aerosol droplets;

to provide an aerosol generating device particularly well-suited for digital measurement of the flow rate of the liquid into and through the device;

to provide a system and process for measuring concentrations of non-volatile residue in test liquids, adapted to facilitate the use of the test liquid as the condensation medium for droplet growth onto previously dried particles for optical detection; and to provide a non-volatile residue measuring system with improved response times for alerting users to changes in non-volatile concentrations, liquid flow rates and other key parameters.

SUMMARY OF THE INVENTION

To achieve these and other objects, there is provided a device for generating an aerosol composed of multiple droplets of a test liquid. The device includes a first conduit for receiving a test liquid at an input flow rate, and a second conduit for receiving pressurized gas. A merger region, open to the first conduit and to the second conduit for simultaneous reception of the test liquid and the pressurized air, is adapted to generate an aerosol composed of multiple droplets of a first portion of the test liquid suspended in the gas. An aerosol exit passage is open to the merger region for conducting the aerosol away from the merger region. A liquid exit passage, open to the merger region, is adapted to conduct an output flow comprised of a second portion of the test liquid away from the merger region. A flow sensor is disposed along the liquid exit passage and adapted to generate a sensor signal indicating an output flow rate of the output flow.

According to this aspect of the invention, the flow rate of ultra pure water into a nebulizer can be determined by measuring the rate at which the nebulizer outputs waste liquid. Measurement occurs at a point downstream of the nebulizer entrance, and is accomplished without contact or other interaction with the nebulizer droplets used to measure residue concentration. Thus, the flow rate measuring component has no impact on residue concentration readings. This approach does not take into account the entire flow of the ultra pure water or other test liquid, although nearly 95 percent of the incoming water becomes waste water. The specific percentage of incoming water that becomes waste water can vary from one nebulizer to another, yet the percentage within any given nebulizer is constant. Consequently, the system can be calibrated to determine the incoming flow rate based on the waste water output flow rate.

Preferably, the first conduit comprises an elongate axially directed flow restricting opening or bore adapted to gradually reduce a pressure of the test liquid in the downstream direction toward the merger region, so that the test liquid enters the merger region at a pressure just above atmospheric pressure. For example, the first conduit can take the form of an extended length of microbore tubing with a restricted (e.g. 500 microns in diameter) axial passage.

The microbore tubing, like the previously used orifice plate, controls the flow rate of the water into the nebulizer, with the added benefit of forming a gradual reduction in water pressure, to just above atmospheric pressure at the nebulizer entrance. With the severe pressure drop at the entrance avoided, gasses dissolved in the ultra pure water tend to remain in solution rather than form gas bubbles. Consequently, downstream disruptions in residue measurements due to gas bubbles are minimized or completely avoided.

Another aspect of the present invention is a droplet generating and flow measuring apparatus. The apparatus includes an input conduit defining an upstream region of a liquid path for conveying a test liquid at an input flow rate. A merger region is open to the input conduit to receive the test liquid for merger with pressurized gas, to generate an aerosol composed of multiple droplets of a first portion of the test liquid suspended in the gas. An aerosol exit passage is open to the merger region for conveying the aerosol away from the merger region. A liquid exit passage, defining a downstream region of the liquid path, is open to the merger region to convey a second portion of the test liquid away from the merger region at an output flow rate. A flow dividing structure is disposed along the liquid path and adapted to separate the test liquid into discrete test liquid segments substantially uniform in volume. A flow sensor is disposed at a sensing location along the liquid path downstream of the flow dividing structure, to detect each of the test liquid segments as it passes the sensing location.

The preferred flow dividing structure is a vessel disposed downstream of the merger region to collect the second portion of the test liquid. The vessel has an orifice at its bottom adapted to serially release the test liquid segments in droplet form. For example, the aerosol generator can be provided with a weir and standpipe arrangement. As water collects in a trap at the bottom of the aerosol generator, it rises above the weir and overflows into the standpipe. A nozzle at the bottom of the standpipe forms the orifice, which is sized to prevent the water or other test liquid from continuously or rapidly draining. Instead, due to surface tension effects, liquid is prevented from leaving the standpipe until the collected liquid reaches a threshold, whereupon the liquid has sufficient weight to overcome surface tension and exits the standpipe as a droplet. If the pressure in the standpipe remains substantially constant, the size of the droplets likewise is constant, and the waste water flow rate is determined by the frequency at which the droplets leave the collection volume. Individual droplets are counted by optical components, to measure waste liquid flow rate and, through calibration, to determine the flow rate of liquid into the nebulizer.

The division of the waste liquid flow into individually counted droplets is particularly well suited for generating digital data. Signals generated when counting the droplets can be provided directly to a digital processor, with no need for an analog-to-digital converter. An additional benefit of this approach is that the droplets exit the nebulizer rather than accumulating within the nebulizer. At the same time, water remains in the trap, weir and standpipe after each droplet leaves the standpipe. The remaining water acts as a seal to prevent outside air from entering the nebulizer. Outside air entry must be prevented, since airborne particles otherwise would mingle with the residue agglomerate particles leaving the nebulizer and cause erroneous residue concentration readings.

Another aspect of the invention is an instrument for measuring non-volatile residue in a test liquid. The instrument includes a conduit arrangement comprising an entrance conduit for conveying a test liquid downstream, and first and second downstream conduits fluid coupled to the entrance conduit for respectively conveying first and second portions of the test liquid. An aerosol generating stage is fluid coupled to the first downstream conduit to receive the first portion of the test liquid, and is adapted to generate an aerosol comprised of multiple test liquid droplets suspended in a gas. An aerosol drying stage is provided downstream of the aerosol generating stage for evaporating the test liquid as the aerosol is conveyed therealong, whereby the aerosol downstream of the drying stage consists essentially of non-volatile residue particles suspended in the gas. A droplet forming stage, downstream of the drying stage, includes a holding component adapted to receive a condensing medium in liquid form and release the condensing medium in vapor form as the aerosol is conveyed therealong, to supersaturate the aerosol and cause droplet growth through condensation of said medium onto the residue particles. A droplet detector is disposed at a sensing location downstream of the droplet forming stage and adapted to detect the droplets resulting from the condensation as they pass the sensing location. The droplet forming stage is coupled to the second downstream conduit to receive the second portion of the test liquid, and to provide the second portion of the test liquid to the holding component as the condensing medium.

In systems used to monitor ultra pure water, this entails the use of water as the working medium in the condensation particle counter. Using water avoids the health and environmental concerns associated with butyl alcohol and other perfluorinated hydrocarbons. This eliminates the need to supply, store and recover such fluids, and to separate such fluids from the ultra pure water. Further, since the ultra pure water being monitored serves as the working medium in the condensation particle counter, the working medium can be supplied and replenished through a direct connection of the CPC to the water supply.

When water is used as the working medium, the aerosol stream is saturated with water vapor and proceeds to a condensing region surrounded by wetted walls that are heated to provide a temperature higher than that of the saturated aerosol stream. Maximum supersaturation occurs at the center of the aerosol flow, because the mass diffusivity of water exceeds the thermal diffusivity of air.

One of the advantages of using water as the working fluid in a CPC is a substantially higher threshold at which spontaneous nucleation (also called homogeneous nucleation) can occur compared with the previously available butyl alcohol based CPC. An improved coincidence correction algorithm in the water-based CPC also contributes to a considerably higher permitted particle/droplet throughput rate. Further, a much shorter drying column and aerosol path from the nebulizer to the CPC considerably reduce diffusion losses and the time elapsed from generating the aerosol to sensing droplets to generate residue concentration information. As a result of these advantages, the concentration information from the CPC is available virtually in real time, and can encompass concentrations ranging from a single part per trillion to 60 parts per billion in the single count mode. If desired, a photometric mode can be employed to increase the upper limit to more than 500 parts per billion.

Another aspect of the invention is a process for determining an input flow rate of a liquid, provided to a nebulizer in a fluid measurement system incorporating the nebulizer and a processor coupled to the nebulizer to receive information from the nebulizer. The process includes:

(a) providing a liquid to a nebulizer at least one known input flow rate;

(b) while so providing the liquid, using the nebulizer to generate an aerosol composed of multiple droplets of a first portion of the liquid suspended in a gas, while conveying a second portion of the liquid along an exit passage of the nebulizer;

(c) measuring a flow rate of the second portion of the liquid to determine an output flow rate corresponding to the at least one known input flow rate;

(d) providing the known input flow rate and the corresponding output flow rate to a processor coupled to the nebulizer; and (e) associating the corresponding output flow rate with the known input flow rate within the processor to enable the processor to generate an indication of the known input flow rate in response to receiving an indication of the corresponding output flow rate from the nebulizer.

The input and output rates may be associated through a calibration process in which several different input rates lead to the measurement of several different output flow rates corresponding individually to the input rates. The rates can be stored to the processor as a look-up table whereby the processor, upon receiving an indication of a measured output flow rate, is caused to generate the corresponding input flow rate.

Alternatively, the input and output flow rates may be associated through a function, e.g. a direct linear function based on a determination that for the nebulizer involved, the output flow rate is a certain percent of the input flow rate.

Yet another aspect of the invention is a process for measuring non-volatile residue concentrations in a monitoring system including an aerosol forming stage and a droplet growth stage downstream of the aerosol forming stage. The process includes:

(a) providing a test liquid flow to a non-volatile residue monitoring system;

(b) using a first portion of the test liquid flow to generate an aerosol composed of multiple droplets of the test liquid suspended in a gas;

(c) drying the aerosol to evaporate the test liquid and thereby provide a dried aerosol consisting essentially of multiple non-volatile residue particles suspended in the gas;

(d) using a second portion of the test liquid flow to supersaturate the dried aerosol and cause droplet growth through condensation of the test liquid onto the non-volatile residue particles; and (e) following the droplet growth, detecting the droplets formed by said condensation to determine a concentration of the non-volatile residue in the test liquid.

Thus, non-volatile residue measuring systems configured according to the present invention generate more reliable concentration information in virtually real time and over a wider range of residue concentrations. The critical flow rate of ultra pure water to the nebulizer is monitored without contacting the ultra pure water used to provide the nebulizer output, and in a manner particularly well suited to generating digital flow rate and concentration data.

IN THE DRAWINGS

For a further understanding of the foregoing features and advantages, reference is made to the following detailed description and to the drawings, in which:

FIG. 1 is a diagrammatic view of a non-volatile residue measuring system configured according to the present invention;

FIG. 2 is a more detailed schematic view of part of the system;

FIGS. 3-5 are sectional views illustrating a nebulizer of the system;

FIGS. 6-9 schematically illustrate the operation of a flow measurement component of the nebulizer; and FIG. 10 is a schematic view of a condensation particle counter of the system.

DETAILED DESCRIPTION OF THE PREFERRED EMBODIMENTS

Turning to the drawings, FIG. 1 is a diagram of a system 16 for monitoring the concentration of non-volatile residue in ultra pure water. The water may be used in a semiconductor fabrication process stage or other application requiring high purity. System 16 continuously monitors the water to insure an acceptably low residue concentration as the water is supplied to the process stage.

As seen in the figure, ultra pure water from a water supply 18 and gas from a compressed air or nitrogen source 20 are supplied to a nebulizer 22 to generate an aerosol including droplets of the water suspended in the air or nitrogen. The aerosol is provided to a condensation particle counter (CPC) 24. Most of the water provided to nebulizer 22, typically close to 95 percent, is not used to form droplets, but instead is provided to a flow sensor 26 used to monitor the flow rate of water into the nebulizer through direct measurement of the waste water flow. The waste water is drained from the nebulizer after flow sensing, as indicated at 28.

The aerosol output of nebulizer 22 is dried to reduce the aerosol to suspended residue particles provided to particle counter 24. As the aerosol travels through the particle counter, it is first saturated, and then channeled through a condensation or supersaturation region in which the residue particles act as nuclei for water condensation. Thus, the residue particles "grow" into considerably larger droplets that are optically detected and counted to generate non-volatile residue concentration information. The concentration information is provided to a microprocessor 30. The microprocessor provides the information to a video display terminal 32 to generate a continuously updated record of non-volatile residue concentration in the ultra pure water. The microprocessor also receives water flow rate information from flow sensor 26.

Particle counter 24 includes an exit 33 through which the aerosol is drawn out of the CPC after the droplets are counted. Water used in the CPC saturation and condensation regions is provided from water supply 18 via a line 34.

FIG. 2 illustrates system 16 in more detail. Ultra pure water from supply 18 is received through a sapphire flow-limiting orifice 36 and delivered to a water pressure regulator 38. Compressed air source 20 provides air under pressure to an air pressure control regulator 40. The air pressure control regulator controls air pressure to the water pressure regulator 38. An air pressure of 30 psi produces a water pressure of 30 psi. A pressure transducer 41 is operably coupled to water pressure regulator 38 to insure maintenance of the desired pressure. The water pressure regulator automatically shuts off the flow of water to downstream system components, which eliminates the potential for water leaks that might occur if the water continued to flow after a loss of the air pressure.

The ultra pure water proceeds through a porous (20-60 micron) sintered steel filter 42 designed to remove coarse material such as plastic fragments, which otherwise might block the flow at downstream components. A 3-way tee 44, downstream of filter 42, incorporates a control orifice having a diameter of 430 micrometers which restricts the water flow to the tee to about 100 milliliters per minute at 30 psi water pressure. Tee 44 divides the ultra pure water flow into a sample flow of about 1 milliliter per minute, and a waste water flow of about 99 milliliters per minute.

A capillary 46 guides the sample flow from tee 44 to an entrance 48 of nebulizer 22. Capillary 46, preferably a section of polytetrafluoroethylene (PTFE) or perfluoroalkoxy (PFA) tubing with a 500 micron axial bore, controls the flow rate of water into the nebulizer, and produces a pressure gradient that reduces the water pressure to just above atmospheric pressure at nebulizer entrance 48.

The water pressure along capillary 46 is reduced gradually and continually over the capillary length in the downstream direction. Thus, for a given capillary inlet water pressure, a longer capillary provides a liquid flow at a lower pressure at the capillary exit (i.e. the nebulizer entrance). In system 16, the preferred length of the capillary is about 9 inches (23 cm). The optimum capillary length can depend on a variety of factors, including water pressure at tee 44, pressure of air entering nebulizer 22, and the exact diameter of the capillary microbore.

In a general sense, capillary 46 provides a flow-controlling conduit to the nebulizer in which the liquid pressure upstream of the nebulizer is reduced, at a rate of at most about one pound per square inch, over each inch of capillary length. More preferably, each inch of capillary length entails a pressure reduction in the range of 0.5-1.0 psi. For example, capillary 46 may reduce the pressure from about 5-10 psi at a point just beyond filter 44 to about 1 psi at the nebulizer entrance. In the preferred approach, the capillary has a uniform diameter axial bore over its complete length, and the desired rate of pressure reduction is achieved over the full capillary length.

With the gradual decrease in water pressure along capillary 46, the tendency for gasses dissolved in the water to form bubbles is substantially eliminated. This avoids a problem in previous residue monitoring systems, in which gas bubbles forming at the nebulizer entrance and then passing through the nebulizer would momentarily disrupt downstream residue measurement. To further reduce this problem, tee 44 is advantageously oriented to direct the sample stream downward while directing the waste water stream upward, whereby any bubbles present in the water tend to rise with the waste stream.

Air from source 20 is provided at about fifty psi to a pressure regulator 50. Downstream, the air passes through a high efficiency particle air (HEPA) filter 52, and then is supplied to a nebulizer air entrance 54 at a pressure of 15 psi and a flow rate of 0.55 liters per minute through a conduit 56. Further, air is provided to a point downstream of nebulizer 22 through a conduit 58. Conduit 58 includes a control orifice 60 for limiting the air flow to a rate of about 2 liters per minute.

Figure 3:
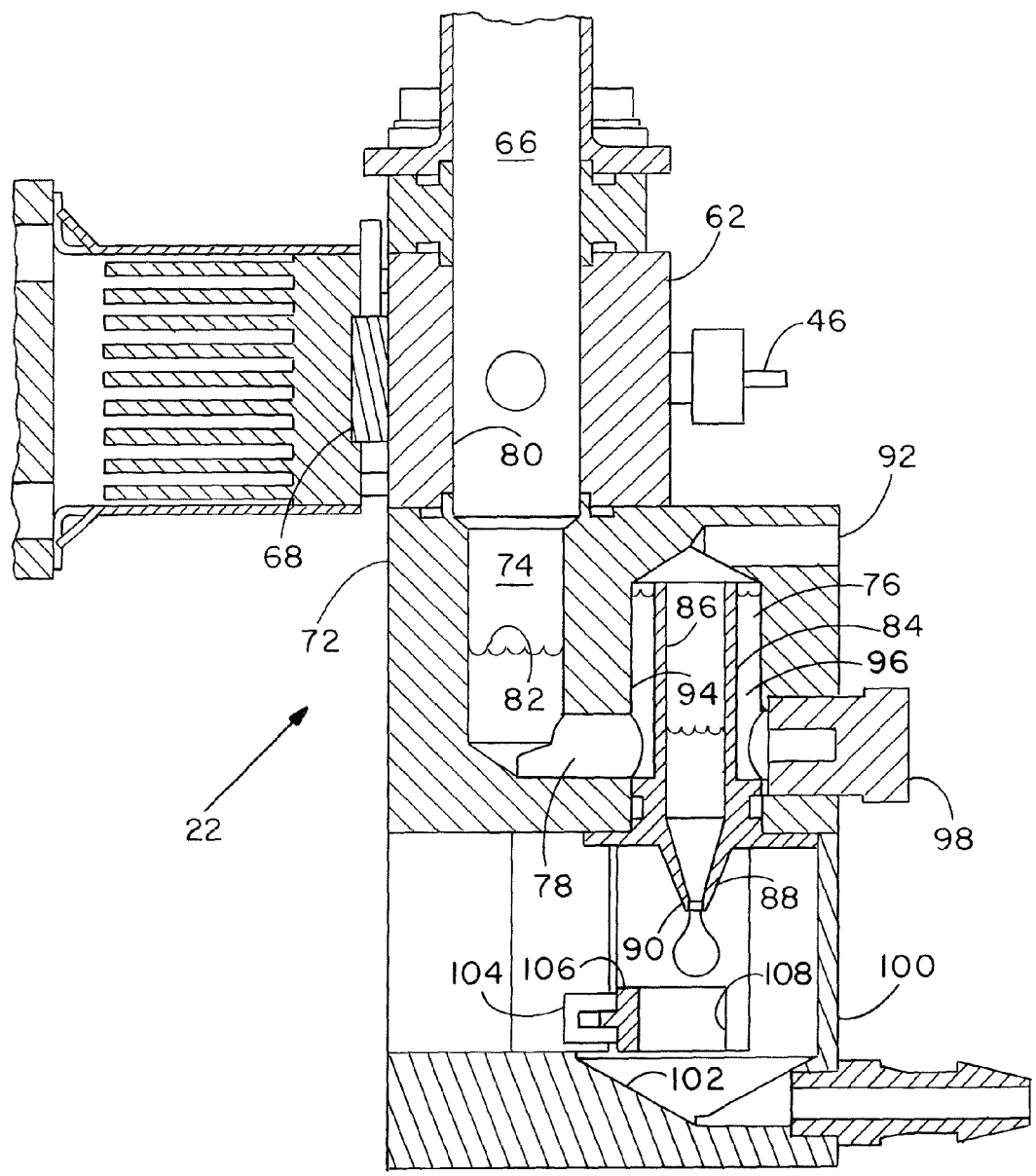
Figure 4:
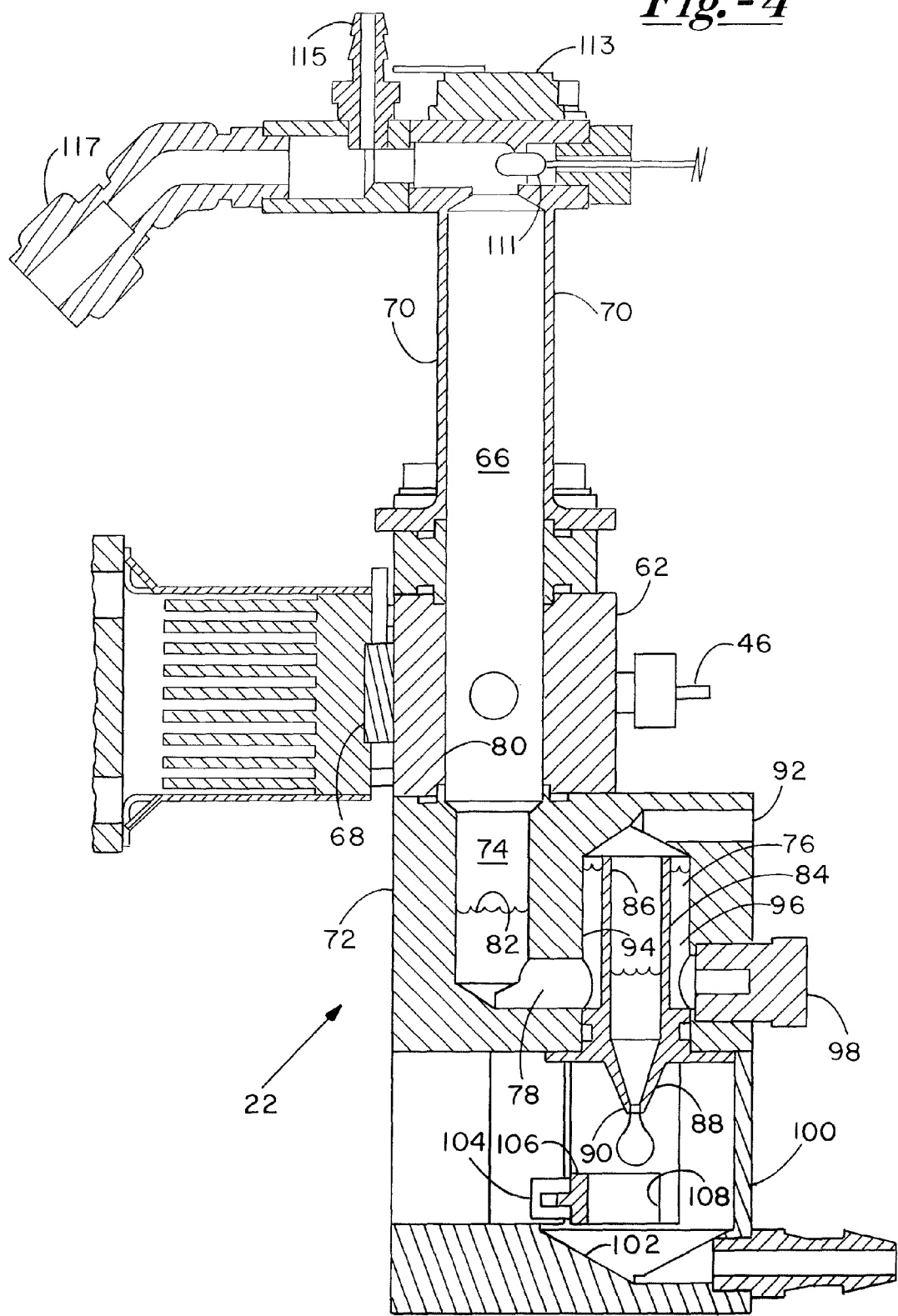
Figure 5:
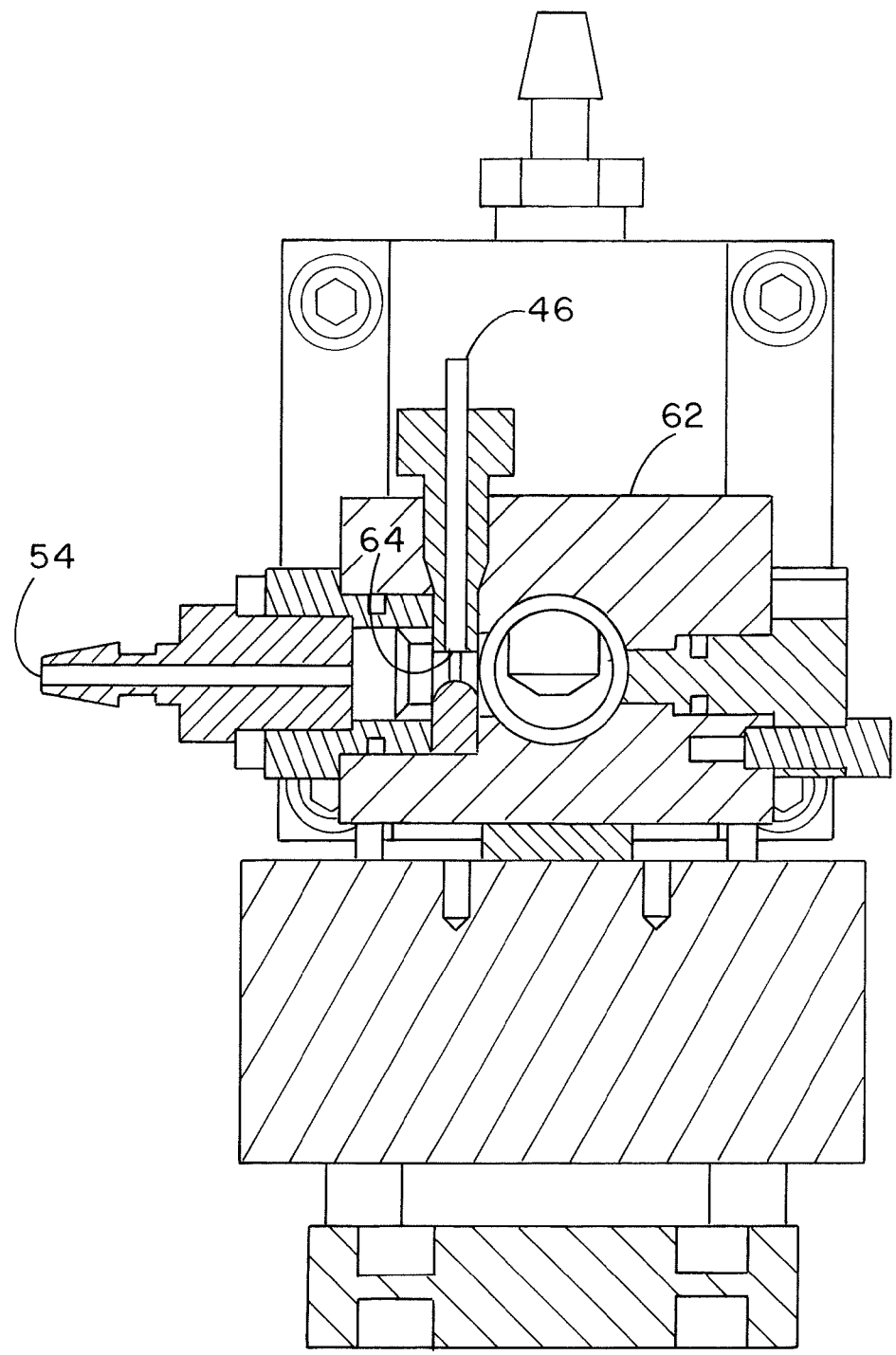

FIGS. 3, 4 and 5 illustrate nebulizer 22 in greater detail. Nebulizer 22 includes a housing section 62 forming a merger region 64 where incoming water and pressurized air mingle to form multiple droplets. The flow of pressurized air into the nebulizer at 54 creates a slightly negative pressure in region 64 that draws water into the nebulizer from capillary 46. The droplets leave nebulizer 22 as an aerosol, traveling upwardly through a passage 66. The proportion of residue relative to water varies with the purity of the water, but is substantially constant over different droplet sizes. Nebulizer 22 generates droplets of different sizes, but there is sufficient consistency in the aggregate such that the droplet count, or more accurately the count of residue particles corresponding to the droplets, is a reliable indicator of non-volatile residue concentration in the water.

A thermoelectric device 68 functions as a heat sink to maintain a stable temperature of about 25° C. in the nebulizer merger region. This promotes more uniform droplet sizes. As the aerosol leaves the nebulizer via aerosol passage 66, a heating element 70 along passage 66 evaporates the water to transform the aerosol into a suspension of residue particles.

A housing section 72 below housing section 62 forms a waste water receiving compartment 74, a downstream holding compartment 76, and a fluid passage 78 located between and coupling compartments 74 and 76. Water not forming the aerosol, i.e. a major portion (e.g. 95 percent) of the water entering nebulizer 22, descends directly into compartment 74, where the water accumulates as indicated at 82.

A water retention vessel 84 includes an upright cylindrical standpipe 86 centered within holding compartment 76, and a truncated conical wall 88 that converges downwardly at about a 60 degree angle to an exit orifice 90.

An upper region of holding compartment 76 is open to atmospheric pressure through a passage 92. A cylindrical interior wall 94 of the holding compartment cooperates with standpipe 86 to form an annular water holding region 96. A plug 98 is removable from housing section 72 to drain the holding region. The hole for plug 98 is also used for machining Waste water at first accumulates in receiving compartment 74, then proceeds through passage 78 to holding region 96. The pressurized air flowing into the nebulizer creates a positive pressure in the receiving compartment. As a result, water in holding region 96 is pushed upwardly until the water level reaches the top of standpipe 86. Further addition of water in receiving compartment 74 causes the water to spill over standpipe 86 into vessel 84. The standpipe thus functions as a weir, with water pushed upwardly and over the top of the weir due to the positive pressure in the receiving compartment.

So long as the levels of water in receiving compartment 74 and holding region 96 are above passage 78, the passage functions as a trap to isolate the interior of vessel 84 from the nebulizer interior, in the sense that the water prevents the direct passage of air or any other gas from one of these regions to the other.

This has several beneficial effects. First, it tends to isolate the vessel interior from any pressure fluctuations in the merger region or elsewhere within the nebulizer. Consequently, the pressure inside vessel 84 is determined by ambient pressure outside of nebulizer 22. The pressure is essentially constant, virtually unaffected by pressure fluctuations inside the nebulizer.

Another benefit is that while the interior of vessel 84 is exposed to ambient air for pressure control, water in holding region 96, passage 78 and receiving compartment 74 prevents ambient air from reaching the nebulizer interior.

Nebulizer 22 includes a fluid flow measuring section 100 disposed below housing section 72 and forming an open region below holding compartment 76. Water leaving vessel 84 through exit orifice 90 descends through the open region to a basin 102, from which the waste water is removed from the nebulizer.

A light emitting diode 104 and a detector 106 are mounted within housing section 100 along the open region. The housing section further includes a reflective surface 108 exposed to the open region and positioned with respect to the diode and sensor such that water descending through the open region passes between the diode and the reflective surface. In the preferred version, this arrangement affords convenient access to the diode and detector. As an alternative, a diode and detector can be placed on opposite sides of the droplet region.

A feature of nebulizer 22 is that waste water is drained through exit orifice 90, eliminating the need to periodically extract waste water from the nebulizer. Further, the waste water is released incrementally, in a manner especially conducive to digital measurement of fluid flow.

Figures 6, 7, 8, 9:
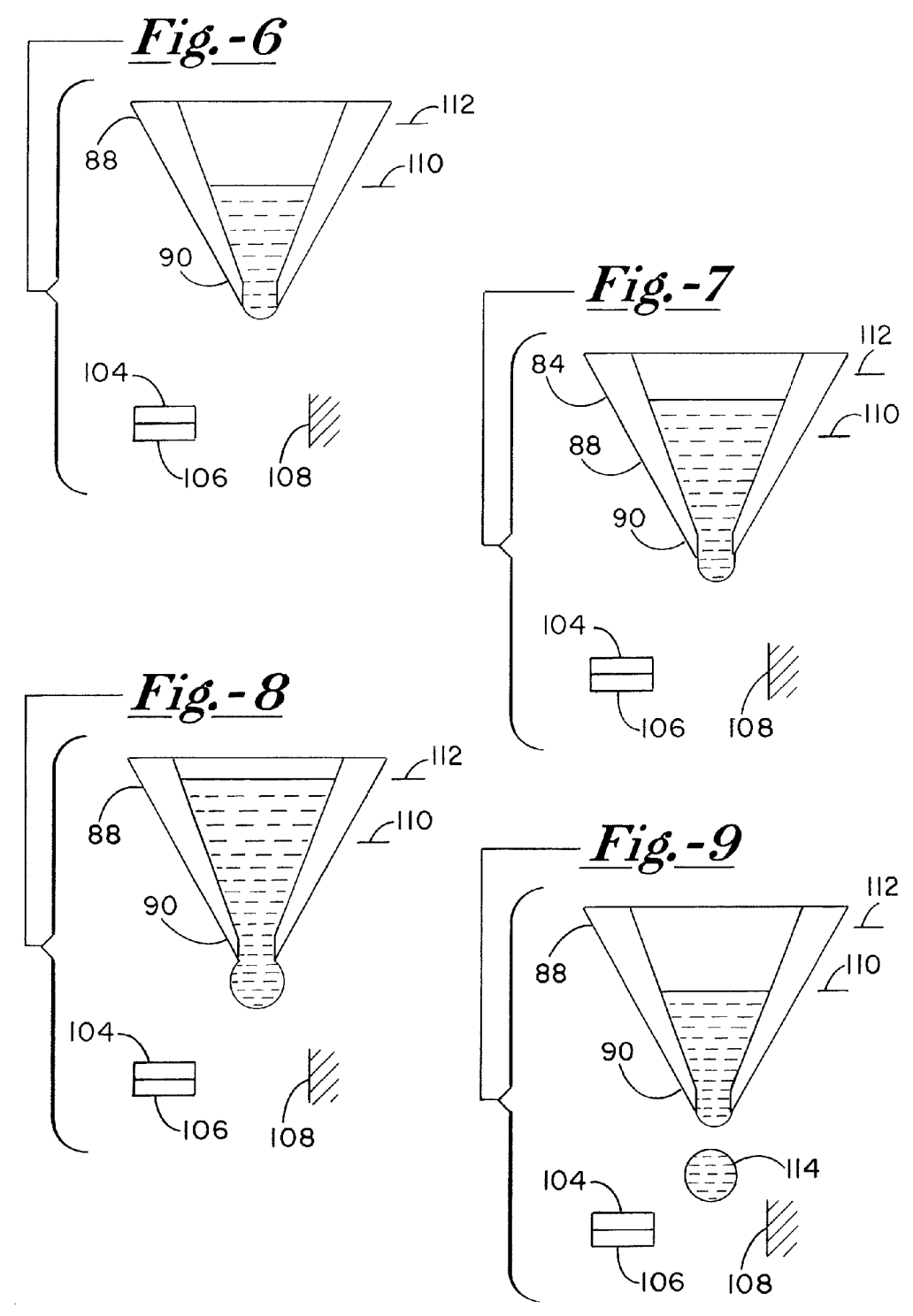

The manner of waste water flow measurement is perhaps best understood from FIGS. 6-9, which schematically show conical wall 88 of vessel 84, diode 104, detector 106 and reflective surface 108. Exit orifice 90 has a diameter (e.g. about 1 mm) selected for temporary retention of water within vessel 84. More particularly, as seen in FIG. 6, water is present in the vessel up to a lower threshold 110. The water is retained by surface tension forces, which at this point overcome the tendency of the water to pass through exit orifice 90 due to gravity.

In FIG. 7, water has accumulated to a level above the lower threshold. Water is suspended below the exit orifice, in an early stage of droplet formation.

In FIG. 8, water has accumulated to the point of reaching an upper threshold 112. At this point, the weight of the water is sufficient to overcome surface tension effects. A droplet 114 is formed and breaks free from the water remaining in the holding component (FIG. 9). When the droplet breaks free, the water level descends to or near to the lower threshold, and the process repeats.

Water overflowing standpipe 86 tends to enter vessel 84 in bursts, intermittently overcoming surface tension to break the meniscus at the top of the standpipe. To modulate these bursts and ensure a more uniform flow of droplets through orifice 90, a piece of felt or natural sponge is inserted into the standpipe.

It has been found that if the positive pressure in vessel 84 is essentially constant (i.e. subject only to changes in atmospheric pressure), the droplets leaving exit orifice 90 are substantially identical in size. As a result, the speed or frequency of droplet formation depends on the rate at which waste water is supplied to the vessel. Thus, the droplet frequency provides a direct measurement of the waste water flow rate.

The dimensions of machined parts and the proportion of incoming water to waste water can vary from one nebulizer to another. Accordingly, nebulizer 22 is calibrated so that the droplet frequency directly indicates the flow rate of ultra pure water into the nebulizer.

Calibration involves supplying water or another liquid to nebulizer 22 at a known constant input flow rate while operating the nebulizer to generate an aerosol. In this manner a portion of the incoming liquid is used to faun the aerosol droplets, while a second portion or remainder of the liquid descends to receiving compartment 74, eventually to exit the nebulizer in the form of droplets 114.

As each droplet 114 descends between diode 104 and reflective surface 108, it momentarily alters the light received by detector 106. In response, the detector provides an electrical pulse or signal to processor 30 via a line 116 (FIG. 1). As noted above, a substantially constant pressure in vessel 84 results in a substantially uniform size in droplets 114. The pulses are counted, and the frequency indicates the waste water flow rate, i.e. an output flow rate corresponding to the known input flow rate.

Calibration entails modifying processor 30 to individually associate a plurality of different output flow rates with a plurality of input flow rates. This can be accomplished by measuring multiple output rates in conjunction with supplying water to the nebulizer at multiple different known input flow rates, to create a look-up table in the processor. Alternatively, based on measuring a single output flow rate for a known input flow rate, or measuring several different output flow rates in conjunction with supplying water at several known flow rates, the user generates a function relating the input and output flow rates. The function may be a direct linear function, e.g. that the output rate is a given fraction or percent of the input flow rate. Or, the function may be more complex. In either event, processor 30 is modified to incorporate the function, and to use the function to generate an indication of the input flow rate responsive to receiving an indication of the output flow rate from the nebulizer.

To this end, and with reference to FIG. 1, processor 30 has a counter register 35 for accumulating a count of pulses from detector 106, and a conversion register 37 in the form of a function or look-up table for determining the input flow rates. Thus, processor 30, based on stored calibration data, generates the fluid flow rate based on the droplet count.

The droplet generation frequency provides an accurate flow rate measurement, despite any fluctuation in the positive pressure in receiving compartment 74. Vessel wall 86 tends to dampen any changes in flow rate due to differences in the positive pressure, smoothing the flow out of exit orifice 90. If desired, the droplet frequency can be used as feedback to adjust the flow rate.

Further, in spite of fluctuations in the positive pressure in compartment 74 or the flow rate into the nebulizer, the water level in compartment 74 prevents ambient air from entering the nebulizer. Water in holding region 96 prevents ambient air from reaching the nebulizer interior via passage 92. Ambient air is kept out of the nebulizer to insure that it cannot mingle with the aerosol, to prevent particles suspended in the air from affecting residue concentration measurement.

As the aerosol stream proceeds upwardly in passage 66, it is heated by heating element 70 to a temperature of 120 degrees to evaporate the ultra pure water, thus transforming the aerosol into a particle suspension rather than a droplet suspension. A thermistor 111 (FIG. 4) monitors the temperature of the air steam as it exits passage 66. The thermistor is used in a control loop to keep the temperature at 120 degrees C. A thermal switch 113 is used to switch off the heater in the event of overheating. Filtered dilution air flowing at a rate of about 2.0 liters per minute enters through a port 115 to lower the dew point. The dried, diluted residue aerosol at a flow rate of about 2.5 liters per minute exits through a fitting 117 and is delivered to the droplet growth stage, condensation particle counter 24.

Returning to FIG. 2, the aerosol path from nebulizer 22 to particle counter 24 is about 18 centimeters in length, as compared to the approximately 80 centimeter path in conventional systems. The shorter aerosol path considerably reduces particle loss due to diffusion. The shorter water pathway coupled with the shorter aerosol pathway also considerably reduces the system response time, to about 90 seconds as compared to nearly ten minutes in conventional systems. Thus, unacceptable concentrations of impurities in the water are determined earlier, and damage can be minimized through more immediate corrective action.

Figure 10:
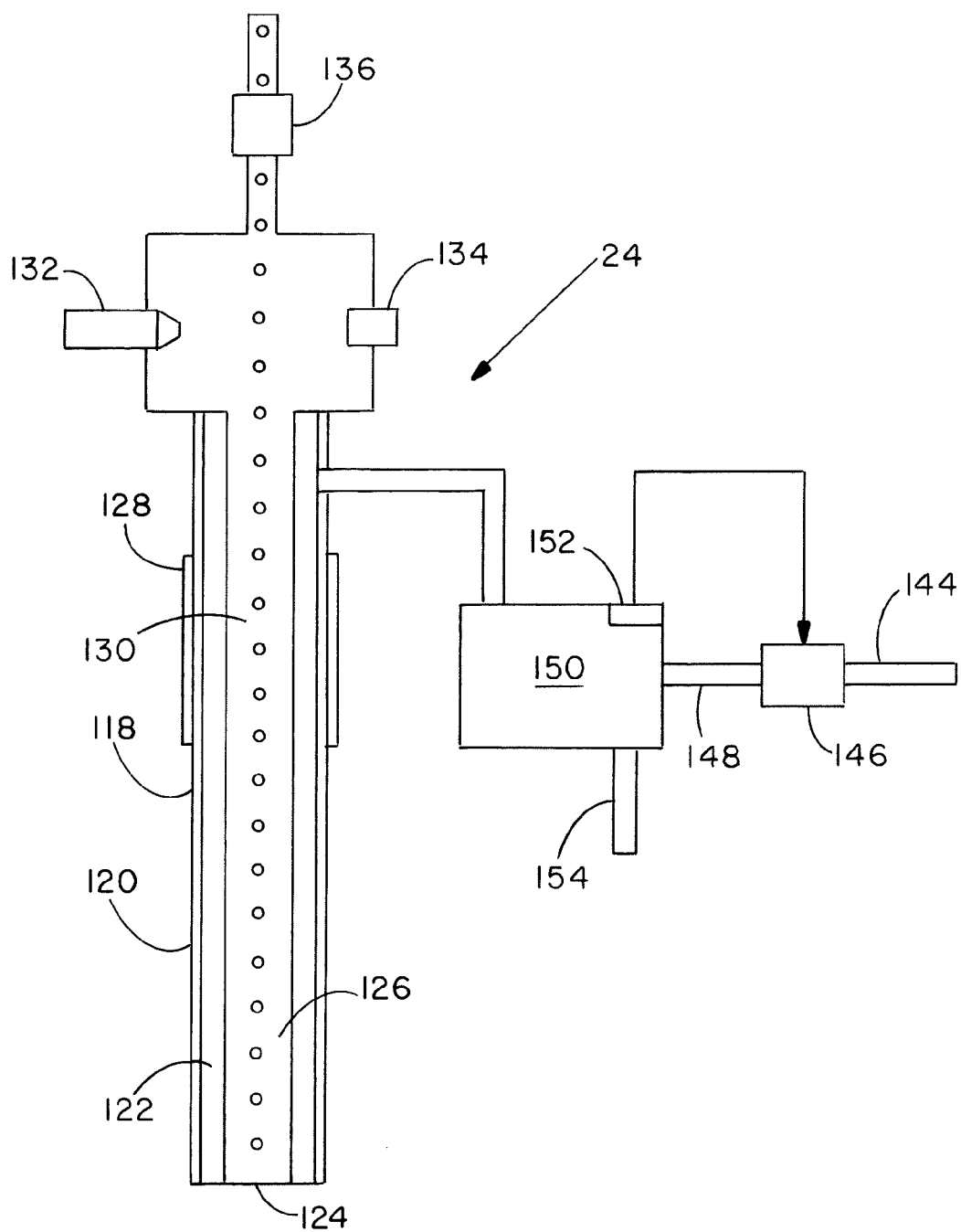

FIG. 10 illustrates condensation particle counter 24 in more detail. The CPC includes a droplet growth column 118 including a substantially rigid cylindrical outer wall 120 and a porous cylindrical inner liner or wick 122. Wick 122, formed of a ceramic material, is adapted to receive and hold water, and thereby provide water vapor to an internal passage 124 surrounded by the wick. If desired, wick 122 can be mounted removably to facilitate inspection and convenient replacement. A lower, saturation region 126 of passage 124 is maintained at a near ambient temperature, e.g. at 20° C. A heating element 128 is used to maintain an upper, droplet growth region 130 of the chamber at an elevated temperature, e.g. 60° C. As aerosol from nebulizer 22 proceeds upwardly through passage 124, it becomes saturated along region 126. As the aerosol travels through region 130, it becomes supersaturated with water vapor. All particles in the aerosol having at least a threshold size of 5 nm become nucleation sites for droplet growth due to water condensation.

As the particles proceed upwardly through growth region 130, two counteracting phenomena are at work. First, due to the elevated temperature the wetted wick generates increased water vapor, which travels radially inward away from the wick toward the center of passage 124. Second, the heated walls tend to transfer heat to the droplet growth region. However, because of the relatively high mass diffusivity of water vapor, the water vapor reaches the center of passage 124 more quickly then the heat. Consequently the particles and their immediately adjacent air, even while being warmed, remain sufficiently cool for supersaturation and the resulting condensation and droplet growth.

A laser diode 132 and light sensor 134 are disposed above droplet growth column 118 on opposite sides of the aerosol stream. Each droplet alters or interrupts light transmission to the sensor to generate an electrical pulse. The pulses are provided to processor 30, and the pulse count yields the non-volatile residue concentration.

Figure 2:
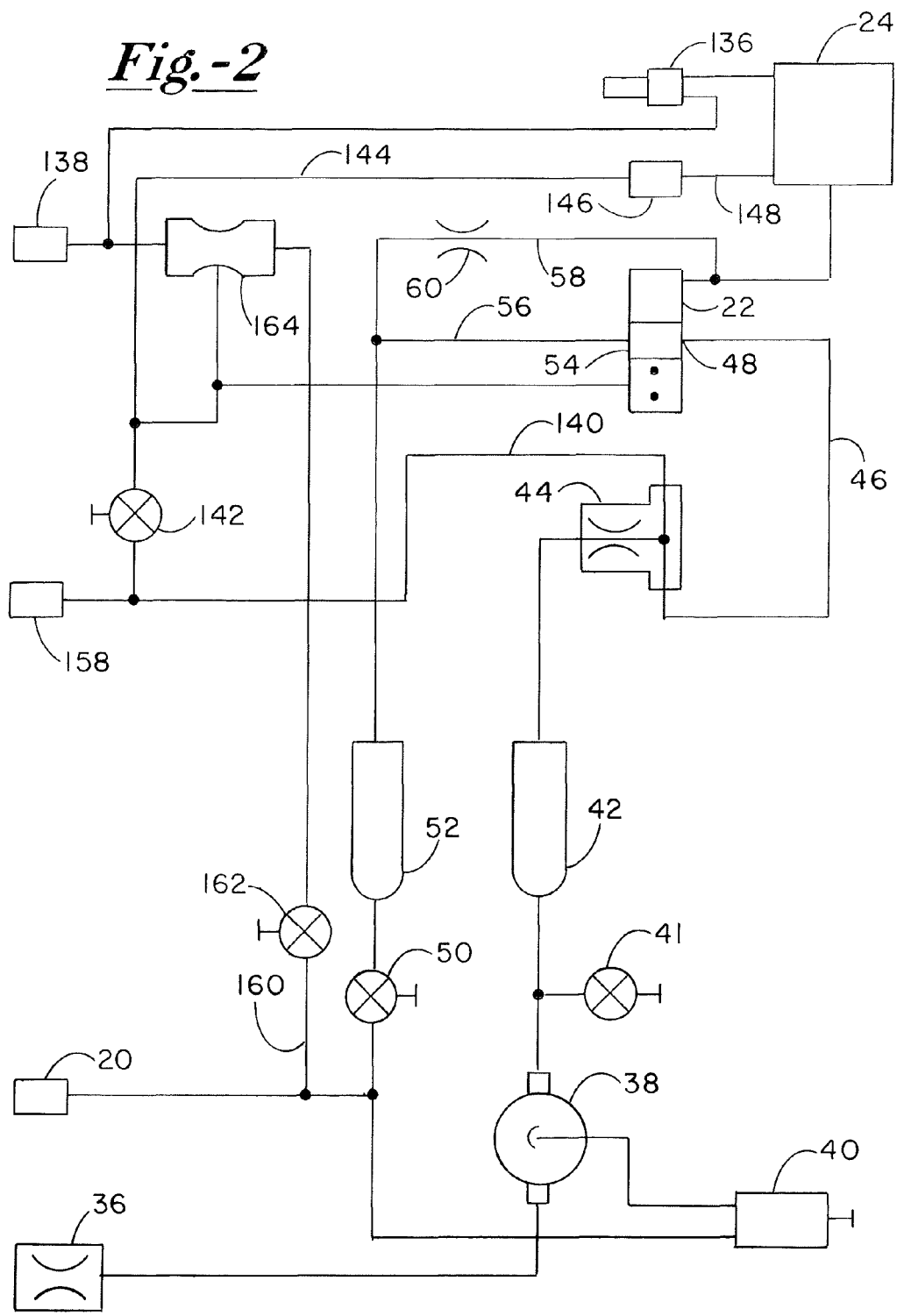

With reference to FIG. 2 as well as FIG. 10, a pump 136 draws the aerosol out of CPC 24 and provides it to a waste outlet 138.

Given the use of water rather than butyl alcohol as the condensation medium, there is no need for equipment designed to supply, circulate and collect the medium and maintain that medium separately from the ultra pure water. Further, the water being monitored can be used as the CPC condensation medium. To this end, as seen in FIG. 2, water from tee 44 not provided to the nebulizer is fluid coupled over a line segment 140 through a backflush valve 142, a line segment 144, a solenoid valve 146 and a line segment 148 to the CPC. In FIG. 1 this is represented by line 34. As seen in FIG. 10, CPC 24 includes a reservoir 150 fluid coupled to the water supply through solenoid valve 146. The solenoid valve normally is closed. When a level sensor 152 in the reservoir senses that the water level in the reservoir has receded below a predetermined threshold, it opens valve 146 to replenish the water supply in the reservoir. Reservoir 150 can be provided with a fitting for draining excess water, as indicated at 154.

Gravity and capillary forces move water from reservoir 150 to wick 122, to insure that the wick remains wetted to provide water vapor along the saturation and growth sections.

Returning to FIG. 2, backflush valve 142 can be closed, and ultra pure water provided in a reverse direction along line 140 from a backflush connection 158. The flow proceeds in the reverse direction through valve 44, filter 42, regulator 38 and inlet orifice 36, to maintain system efficiency by dislodging any blockage that might occur along these components. Compressed air from source 20 not provided to the nebulizer is directed through a conduit 160 and a venturi regulator 162 to a venturi flow guide 164. The air, along with waste water from line 140 and nebulizer 22, is channeled by the venturi guide to waste outlet 138.

Thus, in accordance with the present invention, a system for monitoring non-volatile residue concentrations in ultra pure water generates more reliable information virtually in real time, to facilitate more effective management of processes that depend on water purity. The flow rate of the ultra pure water is measured accurately without contacting water used to generate the sample measurement aerosol, in a manner well suited for generating digital flow measurement data.

What is claimed is:

1. A device for generating an aerosol composed of multiple droplets of a test liquid, including:
    a first conduit for receiving a test liquid at an input flow rate;
    a second conduit for receiving pressurized gas;
    a merger region, open to the first conduit and to the second conduit for simultaneous reception of the test liquid and the pressurized air, adapted to generate an aerosol composed of multiple droplets of a first portion of the test liquid suspended in the gas;
    an aerosol exit passage open to the merger region for conducting the aerosol away from the merger region;
    a liquid exit passage open to the merger region and a measuring section downstream of the liquid exit passage, adapted to conduct an output flow comprised of a second portion of the test liquid away from the merger region; and
    a flow sensor disposed along the measuring section and adapted to generate a sensor signal indicating an output flow rate of the output flow.

2. The device of claim 1 wherein:
    the liquid exit passage incorporates a flow dividing structure adapted to separate the output flow into discrete test liquid segments; and
    the flow sensor is disposed at a sensing location downstream of the flow dividing structure to detect each test liquid segment as it passes the sensing location.

3. The device of claim 2 wherein:
    the flow sensor is adapted to optically detect the test liquid segments and to generate an electrical pulse responsive to each test liquid segment passing the sensing location.

4. The device of claim 2 wherein:
    the flow dividing structure comprises a vessel disposed to collect the output flow, the vessel having an orifice at a bottom thereof adapted to serially release the test liquid segments in droplet form.

5. The device of claim 2 wherein:
    the flow dividing structure further is adapted to separate the output flow into test liquid segments substantially uniform in volume.

6. The device of claim 1 wherein:
    the liquid exit passage comprises a first compartment downstream of the merger region for collecting the output flow, a second compartment downstream of the first compartment, and a wall between the first and second compartments adapted to direct the output flow from the first compartment into the second compartment via spillage over a top of the wall after the first compartment is filled with the test liquid; and
    the second compartment is exposed to ambient pressure, and is substantially isolated from the merger region by the test liquid occupying the first compartment.

7. The device of claim 6 wherein:
the second compartment incorporates structure for releasing the test liquid therefrom in discrete test liquid segments.

8. The device of claim 1 further including:
an aerosol drying stage disposed along the aerosol exit passage for evaporating the first portion of the test liquid, whereby the aerosol downstream of the drying stage is characterized by residue particles suspended in the gas; and
a concentration indicating component downstream of the drying stage and adapted to generate residue concentration information based on received residue particles.

9. The device of claim 1 wherein:
the first conduit comprises an elongate axially directed flow restricting orifice adapted to gradually reduce a pressure of the test liquid in the downstream direction toward the merger region, whereby the test liquid enters the merger region at a pressure just above atmospheric pressure.

10. The device of claim 1 further including:
a processor coupled to receive the sensor signal and adapted to generate an indication of the input flow rate based on the sensor signal.

11. A droplet generating and flow measuring apparatus, including:
an input conduit defining an upstream region of a liquid path for conveying a test liquid at an input flow rate;
a merger region open to the input conduit to receive the test liquid for merger with pressurized gas to generate an aerosol composed of multiple droplets of a first portion of the test liquid suspended in the gas;
an aerosol exit passage open to the merger region for conveying the aerosol away from the merger region;
a liquid exit passage defining a downstream region of the liquid path, open to the merger region to convey a second portion of the test liquid away from the merger region at an output flow rate;
a flow dividing structure disposed along the liquid path and adapted to separate the test liquid into discrete test liquid segments; and
a flow sensor, disposed at a sensing location along the liquid path downstream of the flow dividing structure to detect each of the test liquid segments as it passes the sensing location.

12. The apparatus of claim 11 wherein:
the flow sensor is disposed along the downstream region of the liquid path.

13. The apparatus of claim 12 wherein:
the liquid exit passage comprises a first compartment downstream of the merger region for collecting the second portion of the test liquid, a second compartment downstream of the first compartment, and a wall between the first and second compartments adapted to direct the second portion from the first compartment into the second compartment by spillage over a top of the wall after the first compartment is filled with the test liquid; and
the second compartment is exposed to ambient pressure, and is substantially isolated from the merger region by the test liquid occupying the first compartment.

14. The apparatus of claim 11 wherein:
the flow sensor is adapted to optically detect the test liquid segments and to generate an electrical pulse responsive to each test liquid segment passing the sensing location.

15. The apparatus of claim 11 wherein:
the flow dividing structure comprises a vessel disposed downstream of the merger region to collect the second portion of the test liquid and having an orifice at a bottom thereof adapted to serially release the test liquid segments in droplet form.

16. The apparatus of claim 15 wherein:
the second compartment incorporates the flow dividing structure.

17. The apparatus of claim 11 further including:
a processor coupled to the flow sensor and adapted to generate an indication of the input flow rate based on a frequency at which the flow sensor detects the test liquid segments.

18. The apparatus of claim 11 wherein:
the flow dividing structure is adapted to separate the test liquid into segments substantially uniform in volume.

19. In a fluid measurement system incorporating a nebulizer and a processor coupled to the nebulizer to receive information from the nebulizer, a process for determining an input flow rate of a liquid provided to the nebulizer, including:
providing a liquid to a nebulizer at least one known input flow rate;
while so providing the liquid, using the nebulizer to generate an aerosol composed of multiple droplets of a first portion of the liquid suspended in a gas, while conveying a second portion of the liquid along an exit passage of the nebulizer;
measuring a flow rate of the second portion of the liquid to determine an output flow rate corresponding to the at least one known input flow rate;
providing the known input flow rate and the corresponding output flow rate to a processor coupled to the nebulizer; and
associating the corresponding output flow rate with the known input flow rate within the processor to enable the processor to generate an indication of the known input flow rate in response to receiving an indication of the corresponding output flow rate from the nebulizer.

20. The process of claim 19 wherein:
providing the liquid comprises providing the liquid to the nebulizer at a plurality of different known input flow rates; measuring a flow rate comprises measuring a plurality of different output flow rates, each corresponding to a different one of the known input flow rates;
providing the known input flow rate and the corresponding output flow rate comprises storing the plurality of known input flow rates and their corresponding output flow rates to the processor; and associating the flow rates comprises causing the processor to generate an indication of each one of the known input flow rates in response to receiving an indication of its corresponding output flow rate from the nebulizer.

21. The process of claim 19 wherein:
associating the flow rates comprises determining a function relating the input flow rate and the corresponding output flow rate, and modifying the processor according the function to configure the computer to generate a plurality of different input flow rates, individually, in response to receiving indicia of a plurality of different corresponding output flow rates from the nebulizer.

22. A liquid flow measuring apparatus, including:
structure forming a holding region disposed along a liquid flow path for accumulating liquid received from an upstream region of the liquid flow path;
a vessel disposed downstream of the holding region in fluid communication with the holding region through an interface allowing liquid to flow from the holding region into the vessel responsive to an accumulation of liquid in the holding region exceeding a predetermined threshold, wherein liquid occupying the holding region substantially isolates the vessel from any pressure fluctuations along the upstream region of the liquid flow, the vessel having an orifice adapted to separate liquid exiting the vessel into discrete liquid segments; and a flow sensor disposed along the liquid path at a sensing location downstream of the vessel to detect each of the liquid segments passing the sensing location.

23. The apparatus of claim 22 wherein:

the vessel is exposed to ambient pressure.

24. The apparatus of claim 22 wherein:

the orifice is disposed at a bottom of the vessel to serially release the liquid segments as droplets substantially uniform in volume.

25. The apparatus of claim 22 wherein:

the vessel comprises an upright vessel wall, and the holding region comprises a compartment adjacent the vessel adapted to accumulate liquid to a level coinciding with a top of the vessel wall to determine said threshold whereby liquid exceeding the threshold enters the vessel by spillage over the wall.

26. The apparatus of claim 22 further including:

a processor coupled to the flow sensor and adapted to indicate a flow rate of liquid along the liquid flow path based on a frequency at which the flow sensor detects the liquid segments, wherein the flow sensor is adapted to optically detect the liquid segments and generate an electrical pulse responsive to each liquid segment detected.

27. The apparatus of claim 22 further including:

a housing forming a merger region disposed along the upstream region of the liquid path to receive the liquid for merger with pressurized gas to generate an aerosol composed of multiple droplets of a first portion of the liquid suspended in the gas, an aerosol exit passage open to the merger region for conveying the aerosol away from the merger region, and a liquid exit passage open to the merger region to convey a second portion of the liquid from the merger region to the holding region.

* * * * *